United States Patent [19]

Darby et al.

[11] 4,183,850
[45] Jan. 15, 1980

[54] PROCESS FOR PREPARING 2-ACYLOXYMETHYLPENAMS AND 3-ACYLOXYCEPHAMS

[75] Inventors: Nicholas Darby; Peter K. Wolfert, both of Edmonton, Canada

[73] Assignee: Connlab Holdings Limited, St. Laurent, Canada

[21] Appl. No.: 865,572

[22] Filed: Dec. 29, 1977

[30] Foreign Application Priority Data

Dec. 31, 1976 [GB] United Kingdom ............... 54409/76

[51] Int. Cl.$^2$ ................. C07D 499/04; C07D 501/02
[52] U.S. Cl. .................... 260/239.1; 544/30; 544/28; 424/271; 424/246; 260/239 A
[58] Field of Search ....................... 544/28, 30, 26, 27; 260/239 TB, 239.1 TB; 424/246

[56] References Cited

U.S. PATENT DOCUMENTS

| | | | |
|---|---|---|---|
| 3,668,201 | 6/1972 | Gutowski | 260/243 C |
| 3,668,202 | 6/1972 | Foster et al. | 260/243 C |
| 3,954,732 | 5/1976 | Kamiya et al. | 544/30 |
| 4,029,645 | 6/1977 | Slusarchyk et al. | 544/30 |
| 4,046,761 | 9/1977 | Verweij et al. | 544/30 |
| 4,066,641 | 1/1978 | Hamashima et al. | 544/30 |

FOREIGN PATENT DOCUMENTS 9082691 12/1972 Japan .................... 260/239.1

OTHER PUBLICATIONS

Morin et al., JACS 91 (1969), 1401–1407.
Kukolja et al., JACS 97 (1975), 3192–3198.
Bunce et al., Can. J. Chem. 54 (1976), 2612–2616.
Barton et al., J. Chem. Soc. (C) 1971, 3540–3550.
Micetich, Tetrahedron Letters No. 13, 1976, pp. 971–974.

*Primary Examiner*—Nicholas S. Rizzo
*Attorney, Agent, or Firm*—Cushman, Darby & Cushman

[57] ABSTRACT

A process for preparing 2-acyloxymethylpenams and 3-acyloxycephams of the formulae 1 and 2

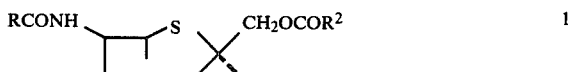

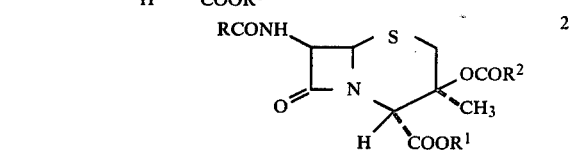

in which R represents the aliphatic, aromatic, or heterocyclic moiety of an amino-protecting group commonly employed in penicillin chemistry, $R^1$ is hydrogen or represents a carboxy-protecting group commonly employed in penicillin chemistry, and $R^2$ is hydrogen, $C_1$–$C_6$ alkyl which may also be substituted with Cl, $OCH_3$, or CN, and phenyl which may also be substituted with $CH_3$, F, Cl, $OCH_3$ or $NO_2$, by treating an unsym-azetidinone disulfide of the formula 3

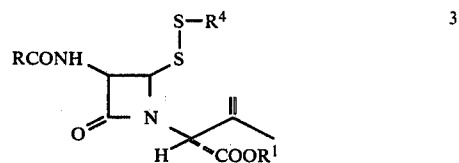

in which R and $R^1$ are as defined above and $R^4$ is benzothiazol-2-yl or benzoxazol-2-yl with silver oxide, an acid of the formula $R^2COOH$, and iodine, or with a silver salt of the formula $R^2COOAg$ and iodine, or with a Simonini complex of the formula $R^2COOI.R^2COOAg$, to obtain a mixture of the compounds of formulae 1 and 2, and optionally separating said mixture.

14 Claims, No Drawings

PROCESS FOR PREPARING 2-ACYLOXYMETHYLPENAMS AND 3-ACYLOXYCEPHAMS

The present invention relates to a process for preparing 2-(substituted methyl)penam derivatives of the formula 1 and 3-substituted-3-methylcepham derivatives of the formula 2, and mixtures thereof,

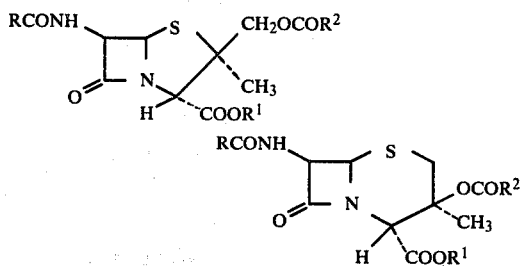

wherein R represents the aliphatic, aromatic or heterocyclic moiety of an amino-protecting group commonly employed in penicillin chemistry and is selected from the group consisting of H; $C_1$–$C_6$ alkyl; phenyl; phenyl substituted in the o-, m-, or p-positions by $CH_3$, F, Cl, $OCH_3$, or a nitro group; benzyl; 2-thienylmethyl; tetrazol-(1-, 2-, or 5-)ylmethyl; phenoxymethyl; $R^3O$ and $R^3S$ wherein $R^3$ represents $C_1$–$C_6$ alkyl, phenyl, benzyl, or trichloroethyl; and 2-phenyl-5-methyl-isoxazol-4-yl; and RCONH may also represent the phthalimido or succinimido group; $R^1$ is hydrogen or represents a carboxy-protecting group commonly employed in penicillin chemistry selected from the group consisting of $C_1$–$C_6$ alkyl, methoxymethyl, phenoxymethyl, benzyloxymethyl, trichloroethyl, benzyl, p-halobenzyl, p-nitrobenzyl, p-methoxybenzyl, benzhydryl, and trimethylsilyl; and $R^2$ is selected from the group consisting of hydrogen; $C_1$–$C_6$ alkyl; $C_1$–$C_6$ alkyl substituted with Cl, $OCH_3$, or CN; phenyl; and phenyl substituted in the o-, m-, or p-positions with $CH_3$, F, Cl, $OCH_3$, or $NO_2$.

The advantages of the process of this invention are the ease with which the products of formulae 1 and 2 may be prepared from readily available starting materials and the excellent yields obtained thereby.

BACKGROUND OF THE INVENTION

A number of processes for preparing certain compounds of formulae 1 and/or 2 have been described in the literature. For example, Morin et al., J. Am. Chem. Soc. 91, 1401 (1969), have shown that treatment of phenoxymethyl penicillin sulfoxide methyl ester with acetic anhydride gave a mixture of the corresponding 2-acetoxymethyl penicillin ester with the corresponding 3-acetoxy-3-methylcepham derivative from which both compounds could be isolated in poor yields by chromatography. Gutowski, U.S. Pat. No. 3,668,201 issued June 6, 1972, has converted certain penicillin sulfoxides by treatment with acids, preferably sulfuric or sulfamic acid or salts thereof, into the corresponding 3-hydroxy-3-methylcepham derivatives, and Foster et al., U.S. Pat. No. 3,668,202 issued June 6, 1972, improved that process by using a tertiary carboxamide containing solvent. Kukolja et al., J. Am. Chem. Soc. 97, 3192 (1975), have shown that 2α-chloromethylpenam derivatives give the corresponding 2α-acetoxymethylpenam derivatives when treated with silver acetate in acetic acid, and that the corresponding 2β-chloromethylpenam derivatives give a mixture of the corresponding 2β-acetoxymethylpenam derivative with the corresponding 3β-acetoxy-3α-methylcepham derivative and the corresponding 3-methylcephem derivative. Kamiya et al., U.S. Pat. No. 3,954,732, issued May 4, 1976, have described, inter alia, the transformation of unsym-azetidinone disulfide derivatives by treatment with various nucleophiles into 2-(substituted methyl)penam and/or 3-substituted-3-(lower alkyl)cepham derivatives. Fujisawa Japanese Patent Publication 9082-691, published August 8, 1974, discloses the reaction of an unsym-azetidinone disulfide with silver acetate in t-butanol to give the corresponding 2-acetoxymethylpenam derivative.

SUMMARY DESCRIPTION OF THE INVENTION

The compounds of formulae 1 and 2 in which R, $R^1$, and $R^2$ are as defined above are prepared according to the process of this invention by treating an unsym-azetidinone disulfide of the formula 3

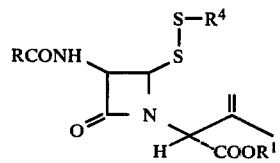

in which R and $R^1$ are as defined above and $R^4$ is benzothiazol-2-yl or benzoxazol-2-yl, prepared according to the method described by Kamiya et al. in Tetrahedron Letters 1973, 3001, with silver oxide in conjunction with an acid of the formula $R^2COOH$ in which $R^2$ is as defined above and with iodine, or with a silver salt of the formula $R^2COOAg$ in which $R^2$ is as defined above and with iodine, or with a Simonini complex of the formula $R^2COOI.R^2COOAg$ in which $R^2$ is as defined above prepared according to the method described by Bunce et al. in Can. J. Chem. 54, 2612 (1976). The reaction is carried out at a temperature within the range of 0°–50° C., preferably at 20°–30° C., and the molar proportions of the compound of formula 3 to silver oxide or silver salt to iodine may vary from approximately 1:1:1 to approximately 1:3:1 depending upon the reactants, and the molar proportions of the compound of formula 3 to Simonini complex may also vary from approximately 1:1 to 1:3. The duration of the reaction may vary from one minute to several hours, and the reaction may be carried out in an inert solvent or a suitable acid of the formula $R^2COOH$ may be used both as reactant and as solvent. After termination of the reaction the mixture may be concentrated under reduced pressure and/or taken up in a water-immiscible solvent, washed with sodium thiosulfate and sodium bicarbonate solutions, dried, and evaporated to a solid foam which is shown by thin layer chromatography (tlc) and by pmr spectroscopy to consist of a mixture of the corresponding compounds of formulae 1 and 2 in which R and $R^1$ are the same as in the starting material of formula 3 and $R^2$ is the same as in the acid of formula $R^2COOH$, in the silver salt of formula $R^2COOAg$, or in the Simonini complex of formula $R^2COOI.R^2COOAg$ used in the above reaction. The ratios in which the compounds of formulae 1 and 2 are present in the above mixture depend upon the reactants used and may vary from about 2:1 to about 1:6 as determined by thin layer chromatography and by pmr spectroscopy.

When it is desired to isolate the individual compounds of formulae 1 and 2 from the above mixture it is advantageous to effect that separation by chromatography, preferably after conversion of the above mixture to a mixture of the corresponding 1β-sulfoxides by treatment with an organic peracid. The individual 1β-sulfoxides of the compounds of formulae 1 and 2 may thus be isolated in the pure state and may be converted back to the corresponding compounds of formulae 1 and 2, respectively, by treatment with phosphorus pentasulfide according to the method described by Micetich in Tetrahedron Letters 1976, 971.

In the above reaction with an organic peracid and the subsequent separation of the 1β-sulfoxides of the compounds of formulae 1 and 2 by chromatography the 3-methylcephem-1β-sulfoxide corresponding to the compound of formula 2 is obtained as a by-product in minor quantities and may be represented by formula 4 in which R and $R^1$ have the same significance as in the respective compound of formula 2

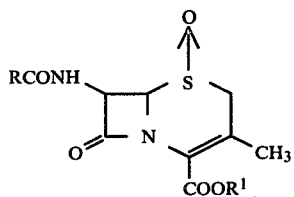

4

The 2-acyloxymethylpenam derivatives of formula 1 have antibacterial activities (see e.g. Barton et al., J. Chem. Soc. (C) 1971, 3540), and the 3-acyloxy-3-methylcepham derivatives of formula 2 are useful as intermediates in the synthesis of biologically active cephem derivatives. For example, a compound of formula 2 in which RCO is an easily removable group or $C_6H_5CH(NH_2)CO$ in which the $NH_2$ group is suitably protected, $R^1$ is an easily removable group and $R^2$ is methyl is treated with a catalyst known in the art to obtain the corresponding 3-methylcephem derivative; replacement of the group RCO by $C_6H_5CH(NH_2)CO$ or deprotection of the $NH_2$ in the latter and removal of the carboxy-protecting group $R^1$ gives the well known antibiotic Cephalexin. Similar uses will be apparent to those skilled in the art.

DETAILED DESCRIPTION OF THE INVENTION

The process of this invention for preparing the compounds of formulae 1 and 2 and mixtures thereof is conveniently carried out as follows.

When it is desired to obtain compounds of formulae 1 and 2 in which $R^2$ is hydrogen or an alkyl or substituted alkyl group having 1-6 carbon atoms as defined above it is preferred to use the acid of the formula $R^2COOH$ both as reactant and as solvent. The unsym-azetidinone disulfide of formula 3 used as starting material is dissolved or suspended in the above acid, silver oxide or a silver salt of the formula $R^2COOAg$ in which the significance of $R^2$ is the same as in the acid of formula $R^2COOH$ is added, and the mixture is agitated for a few minutes until satisfactorily distributed. Iodine is then added, preferably in several successive portions, and the mixture is agitated at 0°–50° C., preferably at 20°–30° C. i.e. at about room temperature, for a period of time ranging from one minute to several hours. Reaction times of rom 1–60 minutes are usually sufficient when using silver oxide, and reaction times of from one to several hours are satisfactory when using a silver salt of the formula $R^2COOAg$. The reaction may also be conducted in an inert solvent such as an aromatic hydrocarbon or a halogenated aliphatic hydrocarbon, with the latter containing preferably 1–2 carbon atoms and 2–4 atoms of chlorine or bromine. After completion of the reaction the mixture may either be evaporated under reduced pressure and taken up in a water-immiscible solvent, or the reaction mixture may be diluted with a water-immiscible solvent, preferably a halogenated aliphatic hydrocarbon as defined above or an aliphatic ether such as diethyl ether. The resulting suspension is filtered from insoluble solids, mainly silver salts, the filtrate is washed with aqueous sodium thiosulfate and sodium bicarbonate solutions, water and/or brine, dried, and evaporated to yield a mixture of the respective compounds of formulae 1 and 2 as the residue.

In the above reaction the ratio of starting material of formula 3 to silver oxide to iodine may vary from 1:1:1 to 1:3:1 on a molar basis, but it is preferred to use a molar ratio of substantially 1:1:1. When conducting the above reaction with a silver salt of the formula $R^2COOAg$ the molar ratio of starting material of formula 3 to silver salt to iodine may vary from 1:2:1 to 1:4:1, but it is preferred to use a molar ratio of substantially 1:2:1. In both cases a molar excess of the acid of formula $R^2COOH$ is preferably used.

The ratio of the compounds of formulae 1 and 2 present in the mixture obtained as described above will vary with the nature of the reactants employed. For example, when using silver oxide or silver acetate in the above reaction together with acetic acid used both as solvent and as reactant the composition of the mixture obtained is about 2.5 parts of the 2-acetoxymethylpenam derivative of formula 1 to about 1 part of the 3-acetoxy-3-methylcepham derivative of formula 2. On the other hand, when using silver oxide and formic acid both as reactant and as solvent in the above reaction, the ratio of the compounds of formulae 1 and 2 in the mixture obtained is about 1 part of the 2-formyloxymethylpenam derivative of formula 1 to about 6 parts of the 3-formyloxy-3-methylcepham derivative of formula 2, with the significance of R and $R^1$ in the formulae of the above products being the same as that in the starting material of formula 3.

When it is desired to obtain compounds of formulae 1 and 2 in which $R^2$ is phenyl or a substituted phenyl group as defined in the first instance it is preferred to use the appropriate Simonini complex prepared in situ according to the method of Bunce et al. cited above and to conduct the reaction in an inert solvent, preferably an aromatic hydrocarbon having 6–8 carbon atoms or an aliphatic halogenated hydrocarbon having 1–2 carbon atoms and 2–4 atoms of chlorine or bromine, or mixtures thereof. In a preferred embodiment of this invention the appropriate Simonini complex is prepared in solution in an aromatic hydrocarbon as defined above from the silver salt of the formula $R^2COOAg$ wherein $R^2$ is phenyl or substituted phenyl as defined above, and iodine. To the solution of the Simonini complex thus obtained there is added a solution of the unsym-azetidinone disulfide of formula 3 selected as starting material in an aliphatic halogenated hydrocarbon solvent as defined above, e.g. methylene chloride, and the resulting mixture is agitated at 0°–50° C., preferably at 20°–30° C. i.e. at about room temperature, for a period of time ranging from one to several hours, preferably for about 4 hours. Filtration of the reaction mixture, washing the filtrate with aqueous sodium thiosulfate, brine and/or water, drying, and evaporating yields a mixture of the corresponding 2-aroyloxymethylpenam derivatives of formula 1 and of the corresponding 3-aroyl-3-methylcepham derivatives of formula 2. The ratio in which the compounds of formulae 1 and 2 are present in the mixture obtained as described above varies again with the nature of the substituent $R^2$ used in the Simonini complex of the formula $R^2COOI.R^2COOAg$. For example, when using the Simonini complex prepared from silver benzoate and iodine the ratio of the 2-benzoyloxymethylpenam derivative to the 3-benzoyloxy-3-methylcepham derivative in the mixture obtained is about 2:1. The preferred molar ratio of starting material of formula 3 to Simonini complex is about 1:2.

The mixtures of the compounds of formulae 1 and 2 obtained by any of the methods described above may be separated into the individual components of formulae 1 and 2 by appropriate means, e.g. by chromatography. However, we have found it to be advantageous to convert the mixtures obtained as described above into mixtures of the corresponding 1β-sulfoxides of the compounds of formulae 1 and 2 before effecting their separation by chromatography. Said conversion of the mixtures obtained as described above to mixtures of the corresponding 1β-sulfoxides is effected by treating the mixtures obtained as described above with an organic peracid in solution in an inert solvent at a temperature within the range of from −30° C. to about 20° C. Preferred conditions include the use of m-chloroperbenzoic acid in solution in an aliphatic halogenated hydrocarbon containing from 1–2 carbon atoms and from 2–4 atoms of chlorine or bromine, e.g. methylene chloride, at about 0° C. for 15–60 minutes, preferably for about 30 minutes, with agitation. Washing of the reaction mixture with aqueous sodium thiosulfate and bicarbonate solutions, brine and/or water, drying, and evaporating yields a mixture of the 1β-sulfoxides of the corresponding compounds of formulae 1 and 2. Said mixture is dissolved in an aliphatic halogenated hydrocarbon as defined above, e.g. methylene chloride, and is separated by chromatography on a suitable adsorbent, e.g. silica gel, by elution with an appropriate solvent, e.g. diethyl ether.

As a by-product of the above reaction there is obtained, in small amounts, the 1β-sulfoxide of the 3-methylcephem derivative corresponding to the 3-acyloxy-3-methylcepham derivative of formula 2. For example, in a typical run using a mixture of methyl 6-phenoxyacetamido-2β-acetoxymethyl-2α-methylpenam-3-carboxylate (1, $R=C_6H_5OCH_2$, $R^1=CH_3$, $R^2=CH_3$) and of methyl 7-phenoxyacetamido-3β-acetoxy-3α-methylcepham-4-carboxylate (2, $R=C_6H_5OCH_2$, $R^1=CH_3$, $R^2=CH_3$) as starting material, converting said mixture to a mixture of the corresponding 1β-sulfoxides by treatment with m-chloroperbenzoic acid, and separating said last-named mixture by chromatography on silica gel using methylene chloride followed by diethyl ether as eluant, the 1β-sulfoxide of the penam derivative of formula 1 was eluted first, followed by the 1β-sulfoxide of the cepham derivative of formula 2 which was found to contain a small amount of the corresponding cephem 1β-sulfoxide of formula 4, methyl 7-phenoxyacetamido-3-methyl-$\Delta^3$-cephem-4-carboxylate-1β-sulfoxide (4, $R=C_6H_5OCH_2$, $R^1=CH_3$); the latter could be separated from the corresponding cepham 1β-sulfoxide by its low solubility in diethyl ether.

The following formulae and Examples, which are explanatory only and not limiting the scope of the disclosure, will further illustrate this invention.

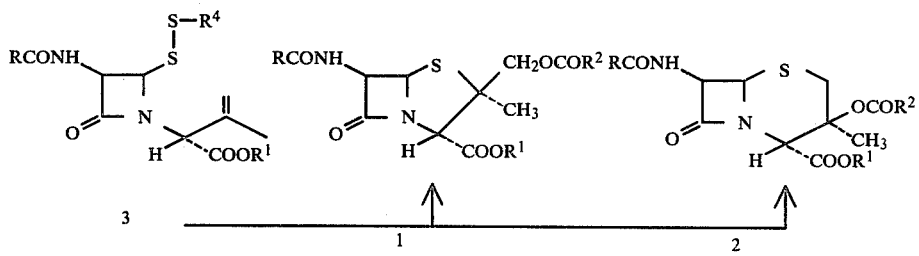

EXAMPLE 1

Methyl 6-Phenoxyacetamido-2β-Acetoxymethyl-2α-Methylpenam-3-Carboxylate, 1 and Methyl 7-Phenoxyacetamido-3β-Acetoxy-3α-Methylcepham-4-Carboxylate, 2, (using silver oxide)

The starting material of formula 3, methyl 3-S-phenoxyacetamido-4-S-(2-benzothiazole disulfide)azetidinone-1-α-propenylacetate (1.14 mmoles) was stirred for five minutes at room temperature with silver oxide (1.14 mmoles) in suspension in acetic acid (10 ml). Iodine (1.14 mmoles) was added to the resulting solution and the mixture stirred an additional 15 mins. at room temperature. The reaction mixture was concentrated in vacuo and the residue triturated well with methylene chloride (5 ml) and ether (20 ml) and filtered through Celite. The filtrate was washed with 10% aqueous sodium thiosulfate (10 ml), then water (3×10 ml), then 5% aqueous sodium bicarbonate (15 ml), then brine (10 ml), and dried over magnesium sulfate. Concentration of the filtrate gave 400 mg (quantitative) of a nearly colourless foam. The tlc and the pmr spectrum confirmed the identity of the above product as a mixture of the title compounds, each of which was found to be identical with an authentic sample. The ratio of the title compound of formula 1 to that of the title compound of formula 2 in the above mixture was found to be about 2.5:1.

In the same manner, but using the trichloroethyl ester of the starting material or the free acid thereof the trichloroethyl esters and the free acids of the title compounds are obtained, respectively.

EXAMPLE 2

Methyl 6-Phenoxyacetamido-2β-Acetoxymethyl-2α-Methylpenam-3-Carboxylate, 1, and Methyl 7-Phenoxyacetamido-3β-Acetoxy-3α-Methylcepham-4-Carboxylate, 2 (using silver acetate)

The same starting material as used in Ex. 1 (10.6 g, 20 mmoles) was suspended in glacial acetic acid (120 ml), silver acetate (6.7 g., 40 mmoles) added and the slurry stirred for 5 mins at room temperature. Iodine (5.08 g., 20 mmoles) was added in portions with stirring over 1 hr, and the reaction mixture stirred an additional hour at room temperature. The brown coloured slurry was diluted with methylene chloride (800 ml) and the insoluble solids (silver salts) removed by filtration. The filtrate was washed with 5% aqueous sodium thiosulfate (200 ml), water (4×100 ml), 5% aqueous sodium bicarbonate (200 ml), brine (2×200 ml) and dried over magnesium sulfate. Concentration of the filtrate gave 10.8 g., of a yellow foam, whose pmr spectrum showed the presence of the 2-acetoxymethylpenam, 1, and the 3-acetoxycepham, 2. The mixture was partially purified by chromatography on silica gel using acetone-hexane (1:2) as eluant to give the mixture of the title compounds in which the individual compounds were characterized by tlc and by pmr spectroscopy and were found to be identical with authentic samples. The ratio of the title compound of formula 1 to the title compound of formula 2 was found to be about 2.5:1.

EXAMPLE 3

Methyl 6-Phenoxyacetamido-2β-Acetoxymethyl-2α-Methylpenam-3-Carboxylate-1β-Sulfoxide and Methyl 7-Phenoxyacetamido-3β-Acetoxy-3α-Methylcepham-4-Carboxylate-1β-Sulfoxide The product from example 2 consisting of the penam-cepham mixture (6.3 g., 14.9 mmole) was dissolved in chloroform (100 ml) and the solution cooled in an ice-bath. m-Chloroperbenzoic acid (3.0 g., 14.9 mmole—85%) was added and the mixture stirred at 0° for ½ hour. The reaction mixture was washed successively with 10% aqueous sodium thiosulfate (30 ml), 5% aqueous sodium bicarbonate (30 ml), brine (30 ml) and then dried over magnesium sulfate. Concentration of the filtrate gave 6.5 g. of a mixture of the sulfoxides (confirmed by tlc and pmr spectroscopy) as a pale yellow foam. Separation and purification was achieved by chromatography on silica gel using methylene chloride followed by ether as eluants.

The methyl 6-phenoxyacetamido-2β-acetoxymethyl-2α-methylpenam-3-carboxylate-1β-sulfoxide, 4.1 g., was first eluted. Further purification was effected by dissolving the white foam in the minimum amount of methylene chloride, cooling the solution to −75° C. and precipitating the compound, as a white solid (3 g.), with ether. The pmr (CDCl$_3$) spectrum: δ1.18 (s, 3H, 2α-C$\underline{H}_3$), 2.03 (s, 3H, OCOC$\underline{H}_3$), 3.78 (s, 3H, COOC$\underline{H}_3$), 4.49 and 4.58 (s, d, 5H, OC$\underline{H}_2$, C$_3$—$\underline{H}$ and 2β—C$\underline{H}_2$OAc), 5.02 (d, 1H, C$_5$—$\underline{H}$), 6.0 and 6.18 (dd, 1H, C$_6$—$\underline{H}$), 6.8 to 7.3 (m, 5H, C$_6$—$\underline{H}_5$), and 8.17 (d, 1H, N$\underline{H}$) is characteristic of this compound.

The later portions consisted of 1.1 g of methyl 7-phenoxyacetamido-3β-acetoxy-3α-methylcepham-4-carboxylate-1β-sulfoxide with a small amount of the cephem sulfoxide. Separation was achieved by the insolubility of the cephem sulfoxide in ether. The pmr (CDCl$_3$) spectrum of the methyl 7-phenoxyacetamido-3β-acetoxy-3α-methylcepham-4-carboxylate-1β-sulfoxide: δ1.65 (s, 3H, C$_3$—C$\underline{H}_3$), 2.10 (s, 3H, OCOC$\underline{H}_3$), 3.65 (ABq, 2H, C$_2$—C$\underline{H}_2$), 3.8 (s, 3H, COOC$\underline{H}_3$), 4.5 (s, 2H, OC$\underline{H}_2$), 4.95 (br, s, 2H, C$_4$—$\underline{H}$ and C$_6$—$\underline{H}$), 5.4 (dd, 1H, C$_7$—$\underline{H}$), 6.8 to 7.65 (m, 6H, C$_6$H$_5$ and N$\underline{H}$) is characteristic and distinct from the penam sulfoxide described above.

The pmr spectrum of the cephem sulfoxide of formula 4 in CDCl$_3$—DMSOd$_6$ was quite distinct and different from the pmr spectra of the penam and cepham sulfoxides described above, and was identical with the pmr spectrum of an authentic sample of methyl 7-phenoxyacetamido-3-methyl-Δ$^3$-cephem-4-carboxylate-1β-sulfoxide prepared by a different route.

EXAMPLE 4

Methyl 6-Phenoxyacetamido-2β-Formyloxymethyl-2α-Methylpenam-3-Carboxylate, 1, and Methyl 7-Phenoxyacetamido-3β-Formyloxy-3α-Methylcepham-4-Carboxylate, 2

A mixture of silver oxide (1 mmole) and the unsymazetidinone disulfide (0.5 mmole) in formic acid (5 ml) was stirred at room temperature and to the resulting stirred solution, a solution of iodine (0.5 mmole) in methylene chloride (3 ml) was added. The mixture was stirred for ½ hr at room temperature, then diluted with methylene chloride (25 ml) and the mixture filtered through Celite. The filtrate was washed successively with 10% aqueous sodium thiosulfate (15 ml), water (2×15 ml), 5% aqueous sodium bicarbonate (15 ml), and brine (10 ml) and then dried over sodium sulfate. Concentration of the filtrate gave a pale yellow foam. This residue was triturated with a little chloroform, and the insoluble portion discarded. The soluble material was obtained after concentration as an almost colourless foam (~80% yield) and consisted of the 2-formyloxymethylpenam, 1, and the 3-formyloxycepham, 2, in a ratio of about 1:6 as determined by pmr spectrography. The signals corresponding to the two title compounds were as follows (CDCl$_3$):

The penam derivative of formula 1 showed δ 1.45 (s), 3.50 (q), 4.75 (s), 5.10 (d), 5.80 (q), 9.1 (s);

The cepham derivative of formula 2 showed δ 1.65 (s), 3.50 (q), 3.75 (s), 4.85 (s), 5.35 (d), 5.65 (q), 8.0 (s).

EXAMPLE 5

Methyl 6-Phenoxyacetamido-2β-Benzoyloxymethyl-2α-Methylpenam-3-Carboxylate, 1, and Methyl 7-Phenoxyacetamido-3β-Benzoyloxy-3α-Methylcepham-4-Carboxylate, 2

The Simonini complex (1.0 mmole) was generated in benzene (9 ml) from silver benzoate (2 mmole) and iodine (1.0 mmole). The unsymazetidinone disulfide (0.5 mmole) in methylene chloride (5 ml) was added, and the mixture stirred for 4 hrs at room temperature. The reaction mixture was filtered through Celite, and the filtrate washed with 10% aqueous sodium thiosulfate (10 ml), then brine (10 ml), and dried over sodium sulfate. Concentration of the filtrate gave a light brown foam. The pmr spectrum of this residue showed it to consist of the 2-benzoyloxymethylpenam, 1, and the 3-benzoyloxycepham, 2, in a ratio of about 2:1. The signals corresponding to the two title compounds were as follows:

The penam derivative of formula 1 showed δ 1.4 (s), 3.50 (q), 4.9 (s), 5.2 (m), 5.8 (m);

The cepham derivative of formula 2 showed δ 1.60 (s), 3.30 (bs), 4.8 (s), 5.2 (m), 5.8 (m).

We claim:

1. A process for preparing a mixture of 2-(substituted methyl)penam and 3-substituted-3-methylcepham derivatives of the formulae 1 and 2

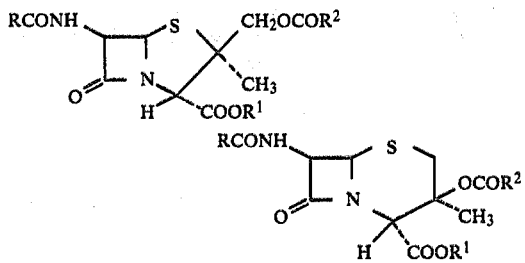

wherein
R represents the aliphatic, aromatic or heterocyclic moiety of an amino-protecting group commonly employed in penicillin chemistry and is selected from the group consisting of H; $C_1$–$C_6$ alkyl; phenyl; phenyl substituted in the o-, m-, or p-positions by $CH_3$, F, Cl, $OCH_3$, or a nitro group; benzyl; 2-thienylmethyl; tetrazol-(1-, 2-, or 5-)yl-methyl; phenoxymethyl; $R^3O$ and $R^3S$ wherein $R^3$ represents $C_1$–$C_6$ alkyl, phenyl, benzyl, or trichloroethyl; and 2-phenyl-5-methyl-isoxazol-4-yl; and RCONH may also represent the phthalimido or succinimido group;

$R^1$ is hydrogen or represents a carboxy-protecting group commonly employed in penicillin chemistry selected from the group consisting of $C_1$–$C_6$ alkyl, methoxymethyl, phenoxymethyl, benzyloxymethyl, trichloroethyl, benzyl, p-halobenzyl, p-nitrobenzyl, p-methoxybenzyl, benzhydryl, and trimethylsilyl; and $R^2$ is selected from the group consisting of hydrogen; $C_1$–$C_6$ alkyl; $C_1C_6$ alkyl substituted with Cl, $OCH_3$, or CN; phenyl; and phenyl substituted in the o-, m-, or p-positions with $CH_3$, F, Cl, $OCH_3$, or $NO_2$, which process comprises treating an unsym-azetidinone disulfide of the formula 3

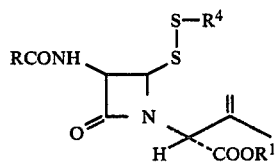

wherein R and $R^1$ are as defined above, and $R^4$ is selected from the group consisting of benzothiazol-2-yl and benzoxazol-2-yl with an agent selected from silver oxide, an acid of the formula $R^2COOH$ in which $R^2$ is as defined above and iodine, a silver salt of the formula $R^2COOAg$ and iodine, in molar proportions of compound of formula 3 to silver oxide or silver salt to iodine of 1:1:1 to 1:3:1, and a Simonini complex of the formula $R^2COOI.R^2COOAg$ in molar proportions of compound of formula 3 to Simonini complex of 1:1 to 1:3, at a temperature within the range of 0°–50° C. for periods of time within the range of one minute to several hours, in an inert solvent selected from an aromatic hydrocarbon or a halogenated aliphatic hydrocarbon containing from 1–2 carbon atoms and from 2–4 atoms of chlorine or bromine, or an acid of the formula $R^2COOH$, and thereafter isolating a mixture of the corresponding penam and cepham derivatives of formulae 1 and 2 in which R, $R^1$ and $R^2$ are as defined above.

2. A process as claimed in claim 1 in which the molar ratio of unsym-azetidinone disulfide of formula 3 to silver oxide to iodine is substantially within the range of 1:1:1.

3. A process as claimed in claim 1 in which the molar ratio of unsym-azetidinone disulfide of formula 3 to the silver salt of formula $R^2COOAg$ to iodine is substantially within the range of 1:2:1.

4. A process as claimed in claim 1 in which the molar ratio of unsym-azetidinone disulfide of formula 3 to Simonini complex of formula $R^2COOI.R^2COOAg$ is substantially within the range of 1:2.

5. A process as claimed in claim 1 in which the reaction between the unsym-azetidinone disulfide of formula 3, silver oxide in conjunction with an acid of the formula $R^2COOH$ or a silver salt of the formula $R^2COOAg$ or a Simonini complex of the formula $R^2COOI.R^2COOAg$, and iodine is carried out at a temperature within the range of 0°–50° C. for a period of time within the range of one minute to several hours.

6. A process as claimed in claim 1 in which the reaction is carried out in an inert solvent.

7. A process as claimed in claim 1 in which the reaction is carried out in an acid of the formula $R^2COOH$ as the solvent.

8. A process as claimed in claim 1 in which methyl 3-S-phenoxyacetamido-4-S-(2-benzothiazole disulfide)azetidinone-1-α-propenylacetate is treated with silver oxide in acetic acid and with iodine, and a mixture of methyl 6-phenoxyacetamido-2β-acetoxymethyl-2α-methylpenam-3-carboxylate and of methyl 7-phenoxyacetamido-3β-acetoxy-3α-methylcepham-4-carboxylate is isolated.

9. A process as claimed in claim 1 in which methyl 3-S-phenoxyacetamido-4-S-(2-benzothiazole disulfide)azetidinone-1-α-propenylacetate is treated with silver acetate in acetic acid and with iodine, and a mixture of methyl 6-phenoxyacetamido-2β-acetoxymethyl-2α-methylpenam-3-carboxylate and of methyl 7-phenoxyacetamido-3β-acetoxy-3α-methylcepham-4carboxylate is isolated.

10. A process as claimed in claim 1 in which methyl 3-S-phenoxyacetamido-4-S-(2-benzothiazole disulfide)azetidinone-1-α-propenylacetate is treated with silver oxide in formic acid and with iodine, and a mixture of methyl 6-phenoxyacetamido-2β-formyloxymethyl-2α-methylpenam-3-carboxylate and of methyl 7-phenoxyacetamido-3β-formyloxy-3α-methylcepham-4-carboxylate is isolated.

11. A process as claimed in claim 1 in which methyl 3-S-phenoxyacetamido-4-S-(2-benzothiazole disulfide)azetidinone-1-α-propenylacetate is treated in solution in methylene chloride with a Simonini complex of the formula $C_6H_5COOI.C_6H_5COOAg$, and a mixture of methyl 6-phenoxyacetamido-2β-benzoyloxymethyl-2α-methylpenam-3-carboxylate and of methyl 7-phenoxyacetamido-3β-benzoyloxy-3α-methylcepham-4-carboxylate is isolated.

12. A process as claimed in claim 1 in which the mixture of 2-(substituted methyl)penam of formula 1 and of 3-substituted-3-methylcepham of formula 2 is separated by chromatography and said 2-(substituted methyl)penam and said 3-substituted-3-methylcepham are isolated, respectively.

13. A process as claimed in claim 12 in which the mixture of 2-(substituted methyl)penam of formula 1 and of 3-substituted-3-methylcepham of formula 2 is treated in solution in an inert solvent with an organic peracid to obtain a mixture of the corresponding sulfoxides, separating said mixture by chromatography, and isolating the corresponding 2-(substituted methyl)penam-1β-sulfoxide, the corresponding 3-substituted-3-methylcepham-1β-sulfoxide, and the corresponding 3-methylcephem-1β-sulfoxide, respectively.

14. A process as claimed in claim 13 in which the mixture of methyl 6-phenoxyacetamido-2β-acetoxymethyl-2α-methylpenam-3-carboxylate and of methyl 7-phenoxyacetamido-3β-acetoxy-3α-methylcepham-4-carboxylate is treated in solution in chloroform with m-chloroperbenzoic acid to obtain a mixture of the corresponding 1β-sulfoxides, separating said mixture by chromatography, and isolating methyl 6-phenoxyacetamido-2β-acetoxymethyl-2α-methylpenam-3-carboxylate-1β-sulfoxide, methyl 7-phenoxyacetamido-3β-acetoxy-3α-methylcepham-4-carboxylate-1β-sulfoxide, and methyl 7-phenoxyacetamido-3-methylcephem-4-carboxylate-1β-sulfoxide, respectively.

* * * * *